United States Patent
Spies et al.

(10) Patent No.: US 7,636,420 B2
(45) Date of Patent: Dec. 22, 2009

(54) RADIO-THERAPEUTIC TREATMENT PLANNING INCORPORATING FUNCTIONAL IMAGING INFORMATION

(75) Inventors: Lothar Spies, Aachen (DE); Matthieu Bal, Aachen (DE); Todd McNutt, Severna Park, MD (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/914,765

(22) PCT Filed: May 1, 2006

(86) PCT No.: PCT/IB2006/051358

§ 371 (c)(1),
(2), (4) Date: Jun. 30, 2008

(87) PCT Pub. No.: WO2006/126109

PCT Pub. Date: Nov. 30, 2006

(65) Prior Publication Data

US 2008/0267351 A1    Oct. 30, 2008

Related U.S. Application Data

(60) Provisional application No. 60/595,005, filed on May 26, 2005.

(51) Int. Cl.
*A61N 5/10*  (2006.01)
*H05G 1/42*  (2006.01)
(52) U.S. Cl. .................................. 378/65; 378/108
(58) Field of Classification Search .............. 378/65, 378/207, 64, 97, 108, 110, 112
See application file for complete search history.

(56) References Cited

U.S. PATENT DOCUMENTS

| 2002/0027971 | A1 | 3/2002 | Deasy et al. |
| 2004/0030246 | A1 | 2/2004 | Townsend et al. |
| 2004/0165696 | A1 | 8/2004 | Lee |
| 2006/0206026 | A1* | 9/2006 | Scarantino et al. .......... 600/436 |

FOREIGN PATENT DOCUMENTS

| WO | 9839736 A1 | 9/1998 |
| WO | 03061466 A2 | 7/2003 |
| WO | 03094695 A2 | 11/2003 |

OTHER PUBLICATIONS

Alber, M., et al.; On biologically conformal boost dose optimization; 2003; Phys. Med. Biol.; 48:N31-N35.

Das, S. K., et al.; Feasibility of optimizing the dose distribution in lung tumors using fluorine-18-fluorodeoxyglucose positron emission tomography and single photon emission computed tomography guided dose prescriptions; 2004; Med. Phys.; 31(6)1452-1461.

(Continued)

*Primary Examiner*—Hoon Song

(57) ABSTRACT

A radiation therapy planning procedure and device provides a model-based segmentation of co-registered anatomical and functional imaging information to provide a more precise radiation therapy plan. The biology-based segmentation models the imaging information to produce a parametric map, which is then clustered into regions of similar radiation sensitivity or other biological parameters relevant for treatment definition. Each clustered region is prescribed its own radiation prescription dose.

21 Claims, 2 Drawing Sheets

OTHER PUBLICATIONS

Kauczor, H.; Multimodal imaging and computer assisted diagnosis for functional tumour characterisation; 2005; Cancer Imaging; 5:46-50.

Ling, C. C., et al.; Towards multidimensional radiotherapy (MD-CRT): Biological imaging and biological conformality; 2000; Int. J. Radiation Oncology Biol. Phys.; 47(3)551-560.

Rajendran, J. G., et al.; Imaging hypoxia and angiogenesis in tumors; 2005; Radiol. Clin. N. Am.; 43:169-187.

Scarfone, C., et al.; Prospective Feasibility Trial of Radiotherapy Target Definition for Head and Neck Cancer Using 3-Dimensional PET and CT Imaging; 2004; J. of Nuclear Medicine; 45(4)543-552.

Thorwarth, D., et al.; A kinetic model for dynamic [18F]-Fmiso PET data to analyse tumour hypoxia; 2005; Phys. Med. Biol.; 50:2209-2224.

Xing, L., et al.; Inverse planning for functional image-guided intensity-modulated radiation therapy; 2002; Phys. Med. Biol.; 47:3567-3578.

Yang, Y., et al.; Towards biologically conformal radiation therapy (BCRT): Selectrive IMRT dose escalation under the guidance of spatial biology distribution; 2005; Med. Phys.; 32(6)1473-1484.

Integration of Functional and Anatomical Brain Images: A Survey of Approaches; Chapter 3; http://www.bic.mni.mcgill.ca/-rik/Phd/pdf-Files/p05ch.3.pdf Mar. 17, 2005.

Miften, M. M., et al.; Incorporation of functional imaging data in the evaluation of dose distributions using the generalized concept of equivalent uniform dose; abstract http://www.iop.org/EJ/abstract/0031-9155/49/9/009 Mar. 17, 2005.

* cited by examiner

RADIO-THERAPEUTIC TREATMENT PLANNING INCORPORATING FUNCTIONAL IMAGING INFORMATION

CROSS REFERENCE TO RELATED APPLICATIONS

This application claims the benefit of U.S. provisional application Ser. No. 60/595,005 filed May 26, 2005, which is incorporated herein by reference.

Radiotherapy is the treatment of diseases, such as cancer tumors, with radiation, such as X-ray radiation. Prior to application of radiation for treatment, a radiation therapy plan must be designed. A radiation treatment plan is used to locate the diseased tissue in amongst the healthy tissue and then focus treatment on the diseased tissue. Radiation applied to healthy tissue can damage the healthy tissue and cause patient side effects. Consequently, the more precise a radiation treatment plan can be the better.

Radiation therapy is an image-guided process whose success critically depends on the precision of the imaging modality. As such, development of a successful radiation therapy plan depends on the level of information that can be ascertained from the imaging information and integrated into the treatment planning process.

Typically, computer tomography (CT) images have been used to provide imaging information for treatment planning. CT images provide anatomical information, which allows for the differentiation of healthy tissue from diseased tissue. CT images further provide the location of critical organs surrounding the diseased tissue. Once the location of the diseased tissue has been determined, a physician manually maps out the contour of the diseased tissue, or target region, and the surrounding organs. A uniform dose of radiation (the prescription dose) is then prescribed to the target region according to clinical experience. Once the prescription dose is prescribed, an optimization procedure is run to obtain the optimal machine settings for the subsequent treatment and the final dose distribution achievable with the optimal machine settings (the application dose).

In recent years, medical imaging has advanced to provide improved information about a region of interest. One such improvement is the incorporation of physiological or functional information obtained by positron emission tomography (PET), single photon emission computed tomography (SPECT), or functional magnetic resonance spectroscopy imaging (MRS). Physicians can use functional information in combination with anatomical information to better define the location and the characteristics of a diseased area. The functional information can provide important information regarding the aggressiveness of the tumor. By providing a kinetic tracer, it can be shown that diseased tissue, such as tumors, may vary in biological function, such as radiation sensitivity across their volume. Consequently, the areas of diseased tissue that are more aggressive may need to be treated with higher levels of radiation in order to eradicate the diseased tissue.

Currently functional imaging information, such as FDG-PET, is being used in radiation therapy planning in two ways. First, the functional imaging information can be used to help demarcate the boundaries of the diseased tissue versus the healthy tissue. Second, the functional imaging information can be used to identify the aggressiveness of different regions of the diseased tissue. By locating the more aggressive areas of the diseased tissue, higher localized radiation doses can be applied to the aggressive areas, while other areas, such as those close to healthy tissue can be given a lower radiation dose. This differentiated radiation dose application allows for aggressive disease tissue to be more heavily targeted and treated, while sparing the surrounding minimally aggressive and healthy tissue areas from the increased dose.

Current use of the functional imaging information is insufficient for multiple reasons. First, most techniques do not incorporate parameters relevant for the definition of the treatment. Often, these parameters need to be extracted from the functional imaging information using physiological or biological models describing the underlying physiological processes. This can lead to inaccurate or imprecise contour demarcation. Second, current techniques do not provide for an automated procedure. Physicians review the functional imaging information and manually draw the contours of the disease tissue and the surrounding organs. Third, current techniques do not account for the noisiness and low contrast of functional imaging information. The noisiness combined with the low contrast poses a major problem, which introduces a high degree of arbitrariness in the planning procedure since areas of different radiation sensitivity cannot be accurately delineated. Furthermore, when noisy image information is fed directly into an optimization process, artifacts can emerge in the application dose. Such artifacts may be the result of instabilities in the optimization process, which is sensitive to noise levels. Instabilities can lead to non-optimal application doses and long processing times.

The present invention is directed to an improved radiation therapy planning procedure and a device for implementing the improved radiation therapy planning procedure. The improved radiation therapy planning procedure incorporates functional imaging information to provide a more precise radiation therapy plan.

In one embodiment, anatomical and functional imaging information are acquired and co-registered. A parametric map based on functional imaging information is derived and used to form clusters of similar radiation sensitivity or other biological information relevant for treatment definition. Each cluster formed has a radiation dose prescribed, which is then optimized by the specific radiation therapy planning device.

In the accompanying drawings, which are incorporated in and constitute a part of this specification, embodiments of the invention are illustrated, which, together with a general description of the invention given above, and the detailed description given below serve to illustrate the principles of this invention. One skilled in the art should realize that these illustrative embodiments are not meant to limit the invention, but merely provide examples incorporating the principles of the invention.

The radiation therapy planning procedure disclosed herein provides an improved method for incorporating functional imaging information to provide more precise radiation therapy plans. In order to better characterize target regions and risk organs with respect to radiation sensitivity, the radiation therapy planning procedure incorporates a biology-based segmentation step that is performed on co-registered anatomical and functional imaging data. The biology-based segmentation step first models the parameters of relevance for radiation therapy planning from functional imaging information resulting in parametric maps. Functional imaging information can be provided as a single image or a set of images from the same modality or different modalities. For the same modality, images can be acquired in a dynamic mode, meaning that a series of images is taken over a longer period of time. Additionally, various contrast agents (or tracers) may be combined. Modeling extracts then the parameter of interest from a single image or multiple images resulting in a better specificity and sensitivity of parametric maps with respect to the relevant biological parameters. The biology-based segmentation step then combines the parametric maps with the anatomical data to cluster the imaged tissue into a user-definable and application-dependent number of tissue classes. Each tissue class has a similar radiation sensitivity, and thus requires, or can tolerate, a similar radiation dose during radiation treatment.

Figure 1:
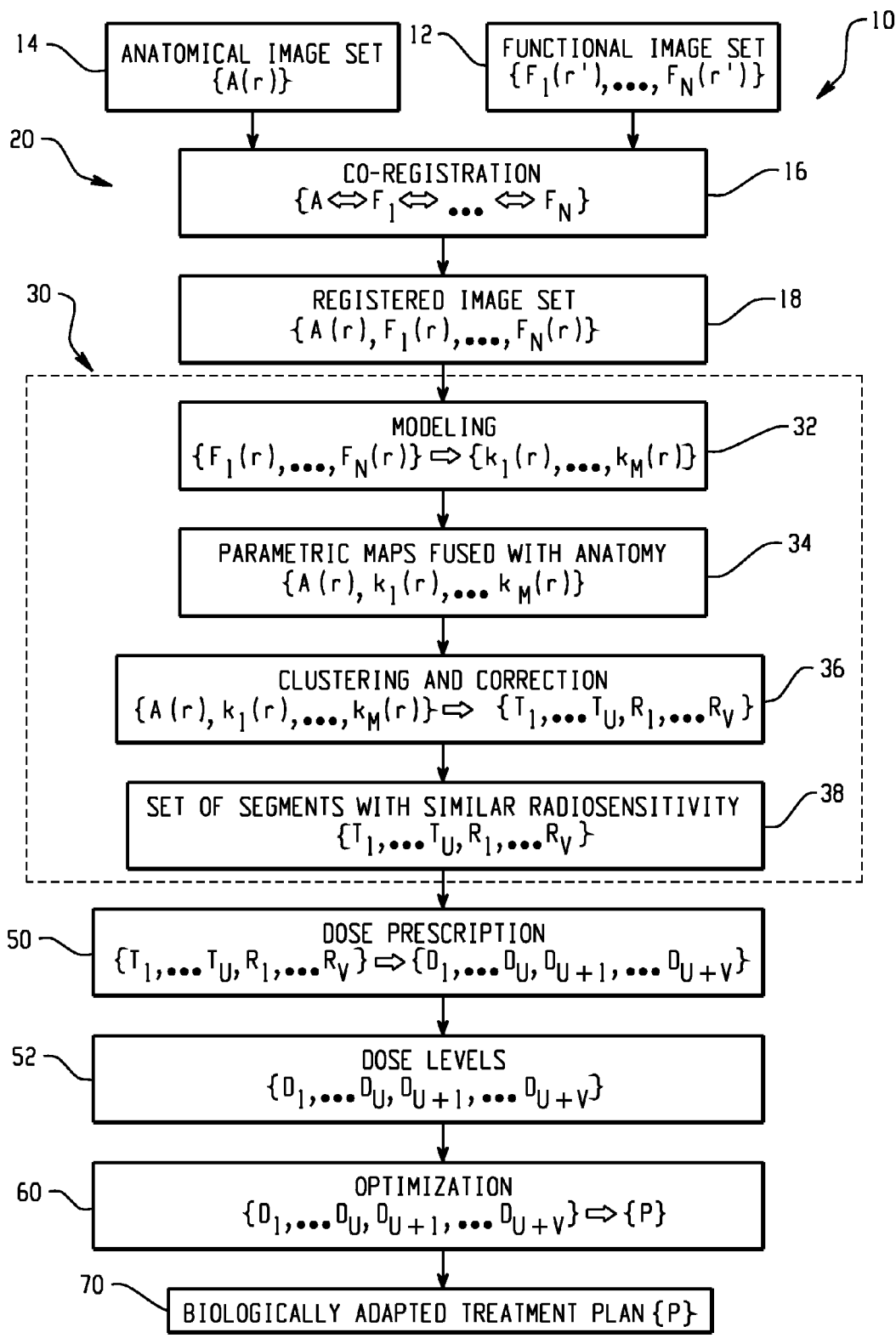
FIG. 1 illustrates a process flow chart for a biology-based segmentation radiation therapy planning procedure.

The radiation therapy planning procedure 10, outlined in FIG. 1, can be segmented into four steps: (1) image acquisition and co-registration 20; (2) biology-based segmentation 30; (3) dose prescription 50; and (4) optimization and application dose determination 60.

The first step in the radiation therapy planning procedure 10 is to acquire functional imaging information F(r') at step 12 and anatomical imaging information A(r) at step 14. The anatomical imaging information can be obtained using any anatomical imaging modality, such as, for example, CT, X-ray, ultrasound, or MRI. The functional imaging information can be obtained using any functional imaging modality, such as, for example, PET, SPECT, gamma detectors, or MRS. The functional image information F(r') and the anatomical image information A(r) are then co-registered at step 16 using techniques to provide a co-registered data set A(r), F(r) at step 18.

Upon completion of the co-registration of the anatomical and functional image information, the radiation therapy planning procedure 10 proceeds to the biology-based segmentation step 30. The biology-based segmentation step 30 can be classified into three sub-steps, namely (1) modeling at 32; (2) clustering at 36; and (3) correction at 36. It should be noted that the correction sub-step, is optional and is operator and procedure dependent.

In the modeling sub-step 32, parameters that are relevant to defining radiation therapy plans, such as, for example, tumor aggressiveness and radiation sensitivity, are modeled. For example, kinetic modeling of time series of functional images enables an accurate quantification of rate constants of physiological processes, such as uptake, trapping or washout of a contrast agent in a given tissue. Compartment modeling is then utilized to extract those rate constants by deploying non-linear regression. In other embodiments, a simple model in which functional data, such as activity maps, are converted into standard uptake values. Use of standard uptake values provides a model that is less dependent on patient weight and other disease independent parameters. However, use of standard uptake value depends on the tracer that is being used as some tracers require more sophisticated modeling techniques. The modeling step 32 results in the creation of a parametric map K(r), which can then be mapped onto the anatomical data A(r) as shown at step 34 and represents the radiation sensitivity distribution across target volume and organs at risk.

At step 36, voxels of the target region and organs at risk are clustered based on location and functionality into classes of similar radiation sensitivity. The total number of classes depends on the noise content and the parameter range of the parametric map. This is because two classes can generally be discriminated in a noisy environment if the difference of the class-representative intensities ΔS is at minimum five times greater than the noise $\sigma_S$. This is based on the model of image detection which states similar criteria for a reliable detection of a uniform object in a noisy background, namely that the ratio of signal difference and noise shall be greater than five, or:

$$\frac{\Delta S}{\sigma_s} \geq 5 \qquad (1)$$

Consequently, the number of classes can be determined in accordance with:

$$\# \text{ classes} = \frac{k_{MAX} - k_{MIN}}{\kappa \cdot \langle \sigma_k \rangle} \qquad (2)$$

in which, $k_{MAX}$ and $k_{MIN}$ are the maximum and minimum parameter value, respectively, of the target volume; $\langle \sigma_k \rangle$ is the standard deviation representative of the noise in the target volume; and κ is a constant with a value of five or greater according to (1). It should be appreciated that κ can be experimentally determined in order to optimize the system.

Figure 2:
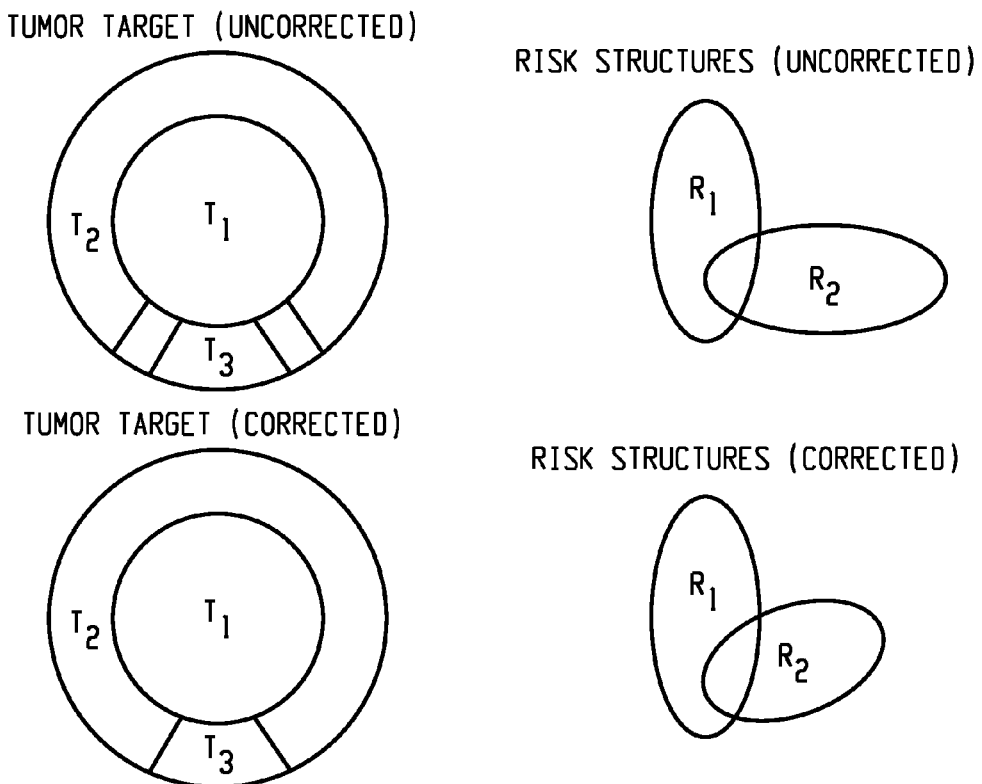
FIG. 2 illustrates a comparison of clustered target regions and surrounding organs at risk before and after correction.

FIG. 2 illustrates a target region that has been clustered into three classes $T_1$, $T_2$, and $T_3$, and organs with two regions $R_1$ and $R_2$ of approximately equal radiation sensitivity. Each of the three classes $T_1$, $T_2$, and $T_3$ comprise regions of the diseased tissue that have similar radiosensitivities. In FIG. 2, $T_1$ represents the necrotic part of the tumor, which is less active and aggressive and thus requires a smaller radiation dose. Conversely, $T_3$ is the most active tumor segment, requiring a high dose boost. The remaining cluster $T_2$ is moderately aggressive and thus needs a medium radiation dose. Typically, the radiation does for cluster $T_2$ is between the maximum dose prescribed for cluster $T_3$ and the minimum dose prescribed for $T_1$ and is sufficient to kill the cells in the cluster.

As further illustrated in FIG. 2, the model-based segmentation radiation therapy planning procedure 10 may optionally include a correction step. Correction of the clusters incorporates prior knowledge through advanced image processing tools, such as morphological operations, and expert knowledge to correct falsely clustered domains. Correction can be automatic, or semi-automatic, to reduce cluster sizes by a predetermined percentage, or can be done manually by the physician via a graphical user interface. As shown in FIG. 2, $T_3$ is reduced about the borders of clusters $T_1$ and $T_2$ to produce a more precise high radiation dose treatment region. The amount of correction, and hence the correction parameters for automatic correction, depend on the noise variance within the clusters of the image. A higher degree of correction may be required as the noise variance $\sigma_k$ approaches or exceeds the parameter difference Δk.

The biology-based segmentation radiation therapy planning procedure 10 then proceeds to step 50, wherein clusters of the same radiation sensitivity are assigned the same dose and tolerance levels. The respective dose levels $D_1 \ldots D_{U+V}$, determined in step 52, can be based on experimental results for known radiation sensitivity or on the physician's knowledge of acceptable prescription doses. A set of look-up tables can be provided to use experimental results as a starting prescription dose, which can then be altered by the physician, if so desired. Alternatively, radiobiological models relating tumor physiology to lethal dose can be used. The prescription doses $D_1 \ldots D_{U+V}$ for the respective clusters $T_1 \ldots T_U$, $R_1 \ldots R_V$ can then be fed into an optimization algorithm at step 60 to determine the application doses for the radiation therapy plan P at 70.

In other embodiments, the functional image information F(r) can be directly incorporated into the optimization process in the form of biological weights, such as, for example, tumor control probability (TCP) and normal tissue complications probability (NTCP), instead of prescribing different dose levels to sub-tumor zones with different radiation sensitivity.

The flowing is an illustrative example of the application of a biology-based segmentation radiation therapy planning procedure, as described above. One should appreciate that the following example is meant solely to provide a working example of the present invention and does not limit the scope of the invention.

Anatomical information can be taken with a CT and co-registered with a time series of FMISO-PET ([$^{18}$F]-fluoromisonidazole) images of a lung cancer tumor. FMISO is a probe that binds selectively to hypoxic cells. Hypoxic cells are those cells that show a deficient level of oxygen, below normal levels. Hypoxic cells tend to be radio-resistant, thus indicating that the cells are more aggressive and will require higher radiation doses.

Figure 3:
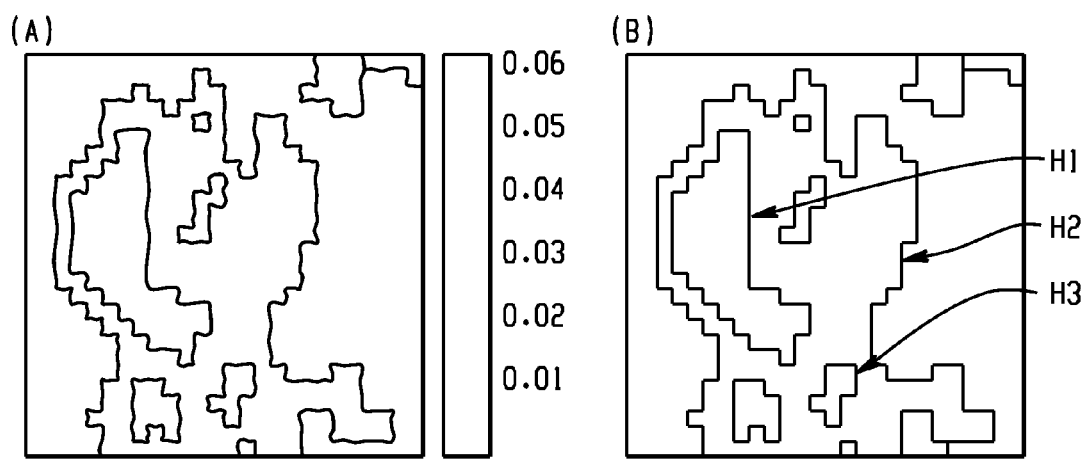
FIG. 3 shows an illustrative example of a parametric map and corresponding radiation sensitivity clustering showing three clusters derived from a biology-based segmentation radiation therapy planning procedure.

Upon completing the acquisition of the co-registered CT and a time series of FMISO-PET image information, a pixel parameter, the net uptake rate of tracer trapped in the tissue, that correlates with the mean oxygen content of the pixel is extracted. The extracted parameter is extracted from the image information using compartmental modeling of time series of FMISO-PET images. The compartmental model is an irreversible two-tissue compartmental model with plasma reference information either taken from blood samples or extracted from a larger blood pool in the image itself. The net uptake rate of tracer trapped in the tissue is given by the tracer flow rate from the first into the second compartment. A parametric map is generated, specifying the level of hypoxia for each voxel of the tumor, and fused with the CT image. The contour of the tumor is outlined using the CT image data. A k-mean classifier clustering technique is performed on the parametric map to cluster the tumor pixels into three classes of hypoxia. As shown in FIG. 3, three clusters are created, a region of high hypoxia H3, a region of medium hypoxia H2, and a region of low hypoxia H1. It should be noted that alternative clustering techniques may be applied, such as, for example, a c-mean classifier, a fuzzy c-mean classifier, or an unsupervised Bayesian classifier. The clusters H1, H2, H3 can then be corrected, if need be. The correction can be done manually by having the physician visually inspect the image and modify the cluster regions via a graphical user interface. In some embodiments, the correction can be done automatically wherein one or more of the cluster regions are reduced by a predetermined percentage, which may be dependent on the noise. The clusters can also be further corrected manually after an automatic correction.

Once the different clusters H1, H2, H3 are formed, the physician prescribes a dose level corresponding to each of the different clusters. The prescribed dose may be determined by experience of the physician or by radiobiological modeling that converts oxygen content of a given cluster into a lethal dose to kill the cells in that particular cluster. The radiobiological modeling may employ look-up tables, which can either be used as the prescribed dose or as a suggested prescribed dose, which can then be modified by the physician. The prescribed dose levels are then fed into an optimization engine of a radiation treatment planning device, such as the PINNACLE™ radiation treatment planning device manufactured by Philips Medical Systems. The optimization planning device factors in the machine parameters to determine the application doses for the respective clustered regions.

The invention has been described with reference to one or more preferred embodiments. Clearly, modifications and alterations will occur to other upon a reading and understanding of this specification. It is intended to include all such modifications and alterations insofar as they come within the scope of the appended claims or equivalents thereof.

The invention claimed is:

1. A radiation therapy planning procedure comprising:
   acquiring anatomical imaging information;
   acquiring functional imaging information;
   co-registering the anatomical and functional imaging information;
   modeling the functional imaging information to create a parametric map;
   clustering segments of the parametric map to form clusters of similar radiation sensitivity or other biological information relevant for treatment definition;
   prescribing a radiation dose to each cluster formed; and
   optimizing the radiation dose of each cluster to provide an application dose for each cluster.

2. The radiation therapy planning procedure of claim 1 further comprising a correction step, wherein the clusters are modified.

3. The radiation therapy planning procedure of claim 2, wherein said correction step includes modifying the size of one or more clusters by a predetermined value.

4. The radiation therapy planning procedure of claim 1, wherein the number of clusters formed is determined by the formula:

$$\# \text{ clusters} = \frac{k_{MAX} - k_{MIN}}{\kappa \cdot \langle \sigma_k \rangle}.$$

5. The radiation therapy planning procedure of claim 1, wherein the radiation dose prescribed for each cluster formed is derived from a look-up table or a radiobiological model.

6. The radiation therapy planning procedure of claim 1, wherein the modeling of the functional imaging information is based on hypoxia.

7. The radiation therapy planning procedure of claim 1, wherein the modeling of the functional imaging information is based upon oxygen content.

8. The radiation therapy planning procedure of claim 1, wherein the number of clusters formed is dependent on the noise.

9. A radiation treatment planning device comprising:
   a means for acquiring anatomical imaging information;
   a means for acquiring functional imaging information;
   a means for co-registering the anatomical and functional imaging information;
   a means for modeling the functional imaging information to create a parametric map;
   a means for clustering segments of the parametric map to form clusters of similar radiation sensitivity;
   a means for prescribing a radiation dose to each cluster formed; and
   a means for optimizing the radiation dose of each cluster to provide an application dose for each cluster.

10. The radiation treatment planning device of claim 9 further comprising a means for correcting one or more clusters.

11. The radiation treatment planning device of claim 10, wherein said means for correcting one or more clusters includes a means for modifying the size of one or more clusters by a predetermined value.

12. The radiation treatment planning device of claim 9, wherein the number of clusters formed is determined by the formula:

$$\text{\# clusters} = \frac{k_{MAX} - k_{MIN}}{\kappa \cdot \langle \sigma_k \rangle}.$$

13. The radiation treatment planning device of claim 9 further including a look-up table that is used to determine the prescribed radiation dose.

14. The radiation treatment planning device of claim 9, wherein the modeling of the functional imaging information is based on hypoxia.

15. The radiation treatment planning device of claim 9, wherein the modeling of the functional imaging information is based upon oxygen content.

16. The radiation therapy planning device of claim 9, wherein the number of clusters formed is dependent on the noise.

17. A radiation therapy planning procedure comprising:
acquiring anatomical imaging information;
acquiring functional imaging information via FMISO-PET;
co-registering the anatomical and functional imaging information;
modeling the functional imaging information based on hypoxia to create a parametric map;
clustering segments of the parametric map to form clusters of similar hypoxia;
prescribing a radiation dose to each cluster formed; and
optimizing the radiation dose of each cluster to provide an application dose for each cluster.

18. The radiation therapy planning procedure of claim 17 further comprising a correction step, wherein the clusters are modified.

19. The radiation therapy planning procedure of claim 17, wherein the number of clusters formed is determined by the formula:

$$\text{\# clusters} = \frac{k_{MAX} - k_{MIN}}{K \cdot \langle \sigma_k \rangle}.$$

20. The radiation therapy planning procedure of claim 1, wherein the number of clusters formed is dependent on the noise.

21. A radiation therapy planning procedure comprising:
modeling the functional imaging information to create a parametric map;
clustering segments of the parametric map to form clusters of similar radiation sensitivity or other biological information relevant for treatment definition;
prescribing a radiation dose to each cluster formed; and
optimizing the radiation dose of each cluster to provide an application dose for each cluster.

* * * * *